United States Patent
Kim et al.

(10) Patent No.: US 8,269,177 B2
(45) Date of Patent: Sep. 18, 2012

(54) MULTIPLEXING READOUT SCHEME FOR A GAMMA RAY DETECTOR

(75) Inventors: Chang Lyong Kim, Niskayuna, NY (US); David McDaniel, Dousman, WI (US); Floribertus P. M. Heukensfeldt Jansen, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 320 days.

(21) Appl. No.: 12/714,529

(22) Filed: Feb. 28, 2010

(65) Prior Publication Data

US 2011/0210255 A1    Sep. 1, 2011

(51) Int. Cl.
G01T 1/166    (2006.01)
(52) U.S. Cl. .................. 250/363.04; 250/367
(58) Field of Classification Search ............ 250/363.03, 250/363.04, 363.09, 366, 367
See application file for complete search history.

(56) References Cited

U.S. PATENT DOCUMENTS

| | | | |
|---|---|---|---|
| 5,391,878 | A | 2/1995 | Petroff |
| 6,114,703 | A | 9/2000 | Levin |
| 7,495,201 | B2 | 2/2009 | Olcott |
| 7,495,222 | B2 | 2/2009 | Zhang |

*Primary Examiner* — Mark R Gaworecki
(74) *Attorney, Agent, or Firm* — Marie Claire B. Maple

(57) ABSTRACT

A method and apparatus for producing a PET image of a tissue using a PET scanner that includes scintillation crystals and detectors. A first crystal group including a first subset of crystals is formed, and a second crystal group including a second subset of the crystals is formed. The crystals in the first crystal group are different from crystals in the second crystal group A first beam striking one or more crystals of the first crystal group is converted to a first electrical signal, while a second beam striking one or more crystals of the second crystal group is converted to a second electrical signal, wherein the second beam is scattered from the first beam. The second electrical signal is corrected using a correction factor derived from at least one of a first and second timing relationships to compensate for energy in the second signal scattered from the first signal. An image of the tissue is created using the corrected second electrical signal.

32 Claims, 6 Drawing Sheets

MULTIPLEXING READOUT SCHEME FOR A GAMMA RAY DETECTOR

FIELD OF THE INVENTION

This invention relates generally to gamma ray detection and in particular to an apparatus and method for correcting for gamma ray scattering in a detector, the correction accomplished using a multiplexing readout scheme.

BACKGROUND OF THE INVENTION

Gamma ray detectors are used in several different applications, including in a positron emission tomography (PET) apparatus. PET is a nuclear medicine imaging technique that produces a three-dimensional image or picture of functional processes within a body. The system detects pairs of gamma rays that are emitted indirectly by a positron-emitting radionuclide (tracer) that is introduced into the body on a biologically active molecule. Images of the tracer concentration in 3-dimensional space within the body are reconstructed by computer analysis. In modern scanners, this reconstruction is often accomplished with the aid of a CT x-ray scan performed on the patient during the same session and using the same apparatus.

To begin the PET imaging process, a short-lived radioactive tracer isotope is incorporated into a biologicaly active molecule and injected into a patient (usually into the blood stream). After a short waiting period, the active molecule concentrates in the tissues of interest and the patient is placed in an imaging scanner. The molecule most commonly used for this purpose is fluorodeoxyglucose (FDG), a sugar labeled with an F-18 isotope with a half life of about 110 minutes.

As the radioisotope undergoes positron emission decay it emits a positron, which is the antiparticle of the electron. After traveling up to a few millimeters within the patient's body, the positron encounters an electron. The encounter annihilates both the positron and the electron, producing a pair of annihilation (gamma) photons that move in opposite directions, i.e., away from each other. The gamma rays are detected when they reach a scintillator in the scanning device, creating a burst of light that is detected by a photo-sensor (e.g., a photomultiplier tube (PMT), a silicon avalanche photodiode or a solid state photomultiplier (SSPM)). Detection depends on simultaneous or coincident detection of the two back-to-back photons, each photon detected by one of two detectors, with the two detectors placed in opposite directions from the annihilation location. Photons that do not arrive in temporal "pairs" (i.e. within a timing-window of few nanoseconds (ns), e.g., less than about 7 ns) are rejected/discarded by the scanner. State-of-the-art scanners are capable of determining the difference in arrival time of the annihilation photons to within about 0.5 ns at full width at half maximum (FWHM).

The radionuclides used in PET scanning are typically isotopes with short half-lives of less than about two hours. For example, an O-15 isotope has a half-life of about 123 seconds and the F-18 isotope referenced above has a half-life of about 110 minutes. These radionuclides are incorporated either into compounds normally used by the body such as glucose (or glucose analogues), water or ammonia, or into molecules that bind to receptors or other sites of physiological significance. Such labeled compounds are known as radiotracers. PET technology can be used to trace the biologic pathway of any compound in living humans provided such compound can be radio-labeled with a PET isotope. When the FDG molecule, an analogue of glucose, is used as the carrier, the imaged tracer concentrations provide information about tissue metabolic activity related to regional glucose uptake. Although FDG is the tracer most commonly used for clinical PET scans, other tracer molecules are used in PET devices to image the tissue concentration of many other molecules of interest.

The PET imaging system comprises, in one embodiment, a plurality of detector rings arranged coaxially to form a cylinder. After receiving the tracer isotope, the patient placed in the cylinder to detect the gamma rays emitted during the annihilation events. FIG. 1 illustrates one such detector ring 10 and a mass or body 12 placed within the ring 10. The ring 10 comprises a plurality of detector blocks 16 that detect gamma rays 20 emitted during annihilation events. The gamma rays travel in opposite directions and strike two oppositely-disposed detectors 20.

FIG. 2 illustrates a perspective view of a plurality of detector rings 10 and detector blocks 16.

FIG. 3 illustrates details of a single block detector 16 comprising a plurality of scintillation crystals 30 that are struck by the gamma rays. A plurality of photomultiplier tubes 34 (vacuum photomultiplier tubes or PMTs) are coupled to the scintillation crystals 30 to detect the light emitted during the scintillation process. FIG. 3 illustrates a 2×2 array of PMTs. A typical block detector comprises an M×N crystal array (with M and N greater than about 6) and a 2×2 array of PMTs (that is, four PMTs). Typically, 40-64 crystals are coupled to the four PMTs.

A one-to-one coupling of the crystals and the PMTs is not possible due to a thickness of the PMT glass. Further, manufacture of a one-to-one coupling block detector is expensive. Thus to reduce the cost and complexity, the 2×2 PMT array determines the incident gamma ray energy and also identifies the crystal in the array that received the gamma ray energy.

Energy deposited in the block detector of FIG. 3 (i.e., energy incident on any of the M×N crystals) is determined and readout by each of the four PMTs in the 2×2 PMT array. The energy in the four PMTs is combined to determine the total incident energy. As is known by those skilled in the art, Anger logic is used to determine the specific crystal that was struck by the incident gamma ray.

Detection by the ring of detectors (as in FIGS. 2 and 3) is based on the concept that two photons detected in close temporal proximity (e.g., within less than about 7 nanoseconds) by the two oppositely disposed detectors) are likely to have originated from a single annihilation event in the patient's body somewhere along a line that connects the two detectors. Such a simultaneous detection is termed a "coincidence." All of the coincidence events detected during an imaging session are recorded by the PET scanner as raw data. As in a single photon emission computed tomography (SPECT), the coincidence data in PET imaging is reconstructed by a computer to produce a three-dimensional image volume.

The electron-positron decays cause the emission of two 511 keV gamma photons at almost 180 degrees apart; hence it is possible to localize their source along a straight line of coincidence (also referred to as a line of response or LOR) connecting the two detected gamma photons. In practice, the LOR has a finite width as the emitted photons are not exactly 180 degrees apart.

If the resolving time of the detectors is greater than about 1 ns, it is difficult to localize the origin of the gamma rays to a segment of the LOR. If the timing resolution is better than about 1 ns, the event can be localized to a segment of the LOR. This localization process is referred to as time-of-flight detection and is used by modern systems with a high timing resolution that can precisely determine the time difference between detection of the photons. These systems thus reduce the length of the LOR segment of interest and more precisely determine the location of the origin of the gamma ray. As the timing resolution improves, the signal-to-noise ratio (SNR) of the reconstructed image also improves, requiring fewer events to achieve the same image quality.

The raw data collected by a PET scanner comprise a list of coincidence events representing near-simultaneous detection of annihilation photons by the pair of oppositely disposed detectors. Using statistics collected from hundred thousands of coincidence events, the most likely activity distribution can be computed using iterative reconstruction techniques known in the art, and thus a map of radioactivities, as a function of voxel (volume element) location parcels is constructed and displayed. The resulting map shows the tissues in which the molecular probe has become concentrated and this map can be interpreted by a nuclear medicine physician or radiologist.

Since the gamma rays are emitted from within the tissue, photon attenuation and absorption in bodily tissue between the annihilation site and the detectors may result in only one of the two photons reaching a detector. These are referred to as "single events" and the data associated with any such single events are discarded. The detection of more coincident events leads to improved sensitivity and resolution of the final image.

A typical PET detector employs a scintillation crystal area of about 4×4 cm$^2$. The crystal area comprises a plurality of crystals, and thus is also referred to as a crystal array. The PET detector further comprises four PMTs (arranged in a 2×2 array), each PMT generating one detector signal. Each PMT is one element of a readout channel. Thus four detector signals (and thus four readout channels) cover the 4×4 cm$^2$ crystal array. A high-gain high-bandwidth amplifier following each PMT amplifies the PMT output signal for input to additional readout/display components.

Photodiodes and solid state photomultipliers (SSPMs) can be used in lieu of the PMTs to detect the light emitted by the scintillation crystals. Since the photodiodes and SSPMs are smaller than the PMTs, they can accommodate a one-to-one coupling with the scintillation crystals. Also, the crystals utilized in an SSPM detector can be smaller than the crystals used with large PMTs, since with direct coupling there is no need to decode the signals from a few PMTs into many crystals; instead there is direct correspondence between the SSPM detector that detects a scintillation, and the crystal in which this scintillation occurred. On the other hand, because SSPMs are smaller than PMTs, many more SSPMs are needed to cover the same detector area. For example, covering a scintillation crystal area of about 4×4 cm$^2$ may require as many as 100 SSPMs, compared with four PMTs.

The additional SSPMs and the one-to-one coupling with the crystals provide considerably improved timing and spatial resolution, but also create problems due to the requirement for higher density in the processing electronics components, resulting in the dissipation of additional power within a smaller space. The smaller area occupied by each crystal may also lead to increased spreading of the incident energy due to scattering (referred to as Compton scattering) from the crystal struck by the incident beam to proximate crystals. Thus although the use of smaller crystals provides better spatial resolution, it also increases the probability of Compton scattering, which leads to a decrease in timing resolution for the crystal signals.

FIG. 4 illustrates a plurality of crystals 48 represented as forming a checkerboard pattern of crystal elements to aid with the description of the invention. As is known by those skilled in the art, each crystal in the array is usually rectangular or square in shape such that a compact array can be formed, although other shapes (for example, hexagonal or triangular) can also be employed to form a compact array.

A gamma ray 50 (an annihilation photon) strikes a crystal 52 with no scattering. i.e., the ray deposits all its energy in the crystal 52. A gamma ray 56 strikes an electron within the crystal 58 and deposits a fraction of its energy there, then impinges a proximate crystal 62 where it deposits the remainder of its energy. This process is referred to as a Compton scattering event. In the latter case the gamma ray energy is absorbed in both the crystal 58 and the crystal 62. Given the conservation of energy principle, the sum of these energies equals the energy in the incident gamma ray. The relative values of these two energies depends on the nature of the collision, the energy of the incident gamma ray, and the mass of the particle struck (an electron) by the incident gamma ray in the crystal 58. Crystal strikes occurring within a predetermined time interval in proximate crystals are assumed to be from the same initial gamma ray. The two strikes will be separated by the time required for the scattered gamma ray to travel from the first crystal to the second crystal.

Two common circuits used to determine the timing of crystal strikes are the leading edge discriminator and the constant fraction discriminator. The leading edge discriminator is a much simpler circuit than the constant fraction discriminator, but the time measured by the leading edge discriminator is dependent on the amplitude of the signal resulting from a strike. The constant fraction discriminator measurement is independent of the signal amplitude. This amplitude dependence is referred to as walk. The energy deposited in multiple crystals from a gamma ray that scattered within the crystal array is less than the initial energy of the gamma ray.

In a one-to-one coupled detector, the walk causes the timing measurements of the strikes in the crystals for a Compton scattering event to be different than the timing that would have been measured if all the gamma ray energy had been deposited in a single crystal. If the signal amplitudes for all the strikes are measured, a correction can be made to eliminate any error in the timing of the strikes due to walk. It should be noted that in a PET scanner using PMT detectors, the timing is measured from the sum of the signals from all crystals and therefore does not contain any errors from Compton scattering walk.

To perform Compton scattering walk correction for a 10×10 crystal-SSPM combination, one-hundred time-to-digital converters (TDCs) are required. The prior art crystal-SSPM combination also requires one-hundred analog-to-digital converters (ADCs) for converting the energy signal to digital values to perform walk correction and obtain accurate timing information from each event. Thus the prior art requires one hundred TDCs and one hundred ADCs to reduce the Compton scattering effects. Each readout channel therefore comprises one crystal-SSPM combination, one TDC and one ADC.

Disadvantageously, using a TDC and an ADC in each readout channel requires an excessive amount of power and for this and other reasons, is not a practical solution. This prior art implementation also requires a substantial space for one hundred TDCs and one hundred ADCs.

To perform the Compton scattering correction, it is necessary to determine for each crystal in which the gamma ray interacted, how much energy was deposited in that crystal and the time that the energy was deposited in the crystal. However, this determination must be made with a limited number of components due to physical space limitations. It is also desired to limit the power consumption/dissipation of these components. The present invention discloses a scheme for satisfying these constraints.

BRIEF SUMMARY OF THE INVENTIONS

One embodiment of the invention comprises a method for producing a PET image of a tissue using a PET scanner, the scanner comprising a plurality of scintillation crystals and a plurality of detectors. The method comprises forming a first crystal group including a first subset of the plurality of crystals; forming a second crystal group including a second subset of the plurality of crystals, wherein crystals comprising the first crystal group are different from crystals comprising the second crystal group; converting a first beam striking one or more crystals of the first crystal group to a first electrical signal; converting a second beam striking one or more crystals of the second crystal group to a second electrical signal, wherein the second beam is scattered from the first beam; determining one or both of a first and a second timing relationship, wherein the first timing relationship is a time interval between a value of the first electrical signal and a time reference, and the second timing relationship is a time interval between a value of the second electrical signal and the time reference; correcting the second electrical signal to produce a corrected second electrical signal using a correction factor derived from at least one of the first and the second timing relationships to compensate for energy in the second signal scattered from the first signal; and creating an image of the tissue using the corrected first electrical signal.

Another embodiment of the invention comprises an apparatus for producing a PET image using a PET scanner. The apparatus comprises scintillation crystals segregated into a plurality of mutually exclusive crystal groups; detectors, one detector coupled to each scintillation crystal, each detector for producing an energy signal responsive to the energy in a gamma ray striking a crystal associated with the detector; comparators responsive to the detectors, each comparator for producing a signal representative of a time when a energy signal crosses a threshold; a number of time-to-digital converters equal to the number of crystal groups, wherein a signal produced by each comparator is supplied as an input to the time-to-digital converter for the respective crystal group for producing a digital timing signal representative of the time when the energy signal crosses the threshold; and a correction element responsive to the energy signal and to the digital timing signal for correcting the energy signal responsive to the digital timing signal.

BRIEF DESCRIPTION OF THE DRAWINGS

The present invention can be more easily understood and the advantages and uses thereof more readily apparent when the following detailed description of the present invention is read in conjunction with the figures wherein.

In accordance with common practice, the various described features are not drawn to scale, but are drawn to emphasize specific features relevant to the inventions. Like reference characters denote like elements throughout the figures and text.

DETAILED DESCRIPTION OF THE INVENTION

Before describing in detail the particular method and apparatus related to PET scanner readout schemes, it should be observed that the present invention resides primarily in a novel and non-obvious combination of elements and process steps. So as not to obscure the disclosure with details that will be readily apparent to those skilled in the art, certain conventional elements and steps have been presented with lesser detail, while the drawings and the specification describe in greater detail other elements and steps pertinent to understanding the inventions.

The presented embodiments are not intended to define limits as to the structures, elements or methods of the inventions, but only to provide exemplary constructions. The embodiments are permissive rather than mandatory and illustrative rather than exhaustive.

As described above, to improve the timing and spatial resolution of a time-of-flight detector, it is preferable to couple one scintillation crystal to one solid state photo-sensor (SSPM), while minimizing scintillation light that spreads to other proximate photo-sensors. While one can design crystal blocks to minimize crosstalk of visible light photons, it is not possible to avoid spreading the light that results from energy being deposited in more than one crystal after Compton scattering. This spreading of light detrimentally affects the final scanned image and the smaller and closer crystals used with SSPMs increase the number of Compton scattering events. Also, using one SSPM for each crystal increases the number of readout channels by more than twenty over a conventional PMT block detector. Thus the power consumption/dissipation per unit volume also increases.

Figure 4:
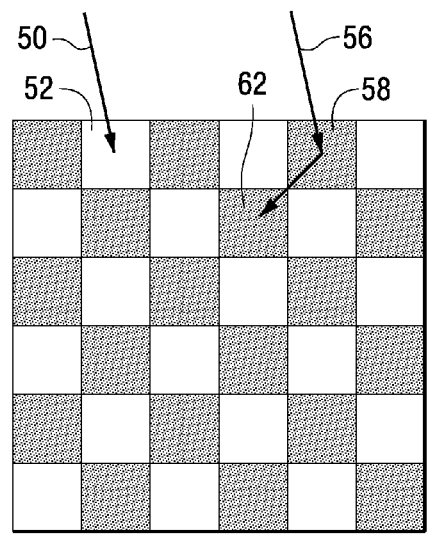
FIG. 4 illustrates a plurality of crystals for receiving impinging gamma rays.

With reference to FIG. 4, one embodiment of the present invention determines the energy deposited in crystal areas 58 and 62 and the variation of those energies with time (i.e., the energy waveform). A correction process, referred to as walk correction for Compton scattering events, employs these parameters to more accurately determine the arrival time of the gamma ray 56. Alternatively, only one of the energies (i.e., the energy deposited in one of the crystals 58 and 62) is required to perform the timing measurement, preferably the greater of the two energies since the timing parameters of interest are more easily and accurately obtained from the energy waveform with the greater magnitude.

The timing of any gamma ray striking a crystal and experiencing Compton scattering can be corrected according to the any one of the various embodiments of the present invention. Also, two gamma rays emitted from the same annihilation event and traveling in opposite directions where they each strike a crystal, can both be corrected according to any one of the various embodiments.

It may not be necessary to correct the gamma ray 50 striking the crystal 52 since there was no Compton scattering. However, it may be desirable to apply walk correction to any event, since there is a finite energy window. But correction is deemed necessary for Compton scattered events. After all the gamma ray arrival times are determined, with any scattered rays corrected before determining the arrival time, the arrival times of all the gamma rays are analyzed to determine gamma rays that originated from the same annihilation event. Once these coincident events have been determined, a more accurate image of the radioactivities within the tissue of interest can be created.

To overcome the Compton scattering effects associated with the use of SSPMs and the one-one coupling of a crystal and an SSPM, the present invention employs a multiplexing scheme utilizing a fewer number of TDCs (and TDC amplifiers, with one amplifier associated with each TDC) than required by the prior art. This scheme reduces the power dissipation and the physical space required for the TDCs, while acquiring and retaining the signal timing information to allow Compton scattering correction. To save space and reduce power consumption/dissipation, it is also desired to reduce the number of ADCs by using a multiplexing scheme.

Also, in digitizing the timing information (in the TDC) and the amplitude information (in the ADC) a lower sampling rate can be used for the ADC (e.g., 10 MHz for the ADC versus 100 MHz for the TDC) to reduce the power consumed by the ADCs, since the timing information associated with the energy information produced by the ADC is not critical. A TDC with greater timing resolution requires more power, which must be dissipated from the TDC. Thus the inventive multiplexing scheme of the present invention is particularly advantageous.

Most of Compton scattered photons strike an area proximate the crystal impinged by the initial or incident gamma ray. As distance from this crystal increases, the probability that a scattered gamma ray will interact with a more distant crystal declines. This phenomenon of proximate scattering is due, at least in part, to the high stopping power of crystals in the state-of-the-art SSPM PET scanners.

A technical effect of the various embodiments of the present invention is the multiplexing of the respective timing and energy signals to reduce the number of TDCs and ADCs, while maintaining the walk correction capability for Compton scattering. This multiplexing scheme permits the use of a number of TDCs and ADCs less than the number of crystal-SSPM combinations and less than the number of TDCs and ADCs used in the prior art schemes.

Walk correction improves the timing resolution for Compton scattered events. The number of Compton scattering events depends on crystal size, as well as the stopping power of each crystal. As related to crystal size, if a scattered gamma ray travels, for example, about 2 mm and the crystal size is about 4 mm thick, the Compton scattered event cannot be detected since all energy (both the incident ray and the scattered ray) impinges on the same crystal. Thus according to this scenario only scattering events that occur near the crystal surface result in Compton scattering, i.e., scattering to another crystal.

The stopping power of each crystal is directly related to the density or mass of the crystal material (i.e., the density of electrons in the crystal material and the binding energy between the atomic nucleus and the electrons, heavier atoms having a higher binding energy). According to the principles of conservation of momentum and energy, when a gamma ray undergoes an elastic collision with an electron in a high density crystal material, some fraction of the energy is transferred to the crystal material. The remainder of the energy is carried off by the scattered gamma ray. The distance traveled by the scattered gamma ray (i.e., the gamma ray resulting from Compton scattering) is directly related to the energy of the scattered ray. For example, assume an incident 511 keV gamma ray deposits some energy in the crystal material and the scattered ray energy is 400 keV. The average distance traveled by the 400 keV ray will be shorter than the average distance traveled by the 511 keV ray. Typically, a crystal comprising low Z (atomic number) material generates more Compton scattering events and the scattered rays travel a longer distance before stopping.

Figure 5:
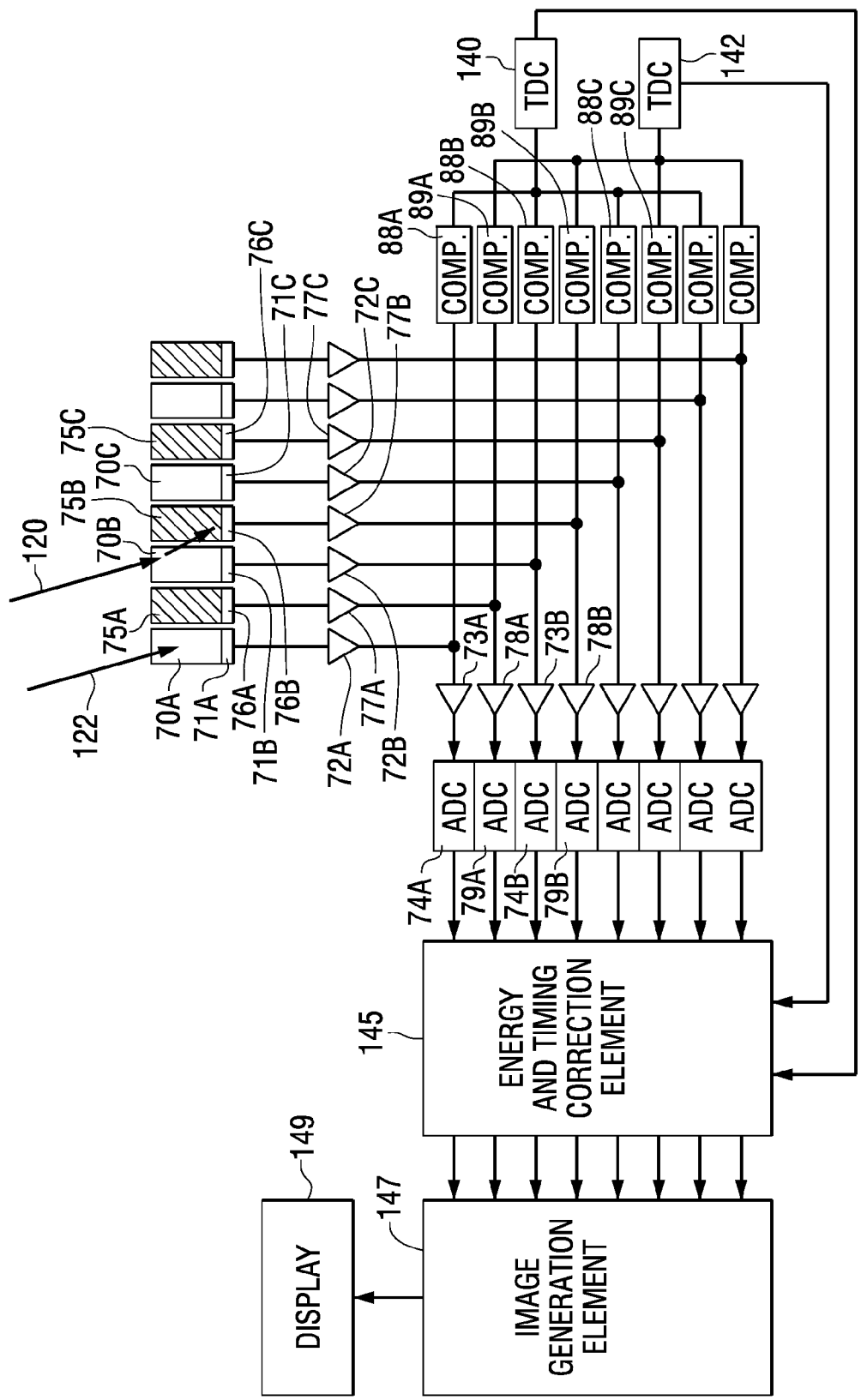
FIG. 5 illustrates signal processing components for SSPM detectors.

FIG. 5 illustrates a readout scheme for an array of scintillating crystals coupled to SSPMs. Although FIG. 5 illustrates the crystals arranged in a single row to, they can be considered as arranged in a checkerboard pattern, as illustrated in FIGS. 4 and 7-9, to simplify the explanation of the present invention. The linear arrangement illustrated in FIG. 5 shows only the pertinent elements and interconnections of those elements. Generally, the components on the left side of FIG. 5 generate energy signals representative of the received gamma rays, and the components on the right side of FIG. 5 generate timing signals that are used to correct the energy signals by removing the Compton scattering effects.

The light produced by crystals 70A, 70B, 70C, etc. (when struck by a gamma ray) is detected and a signal representative thereof is produced by an associated SSPM 71A, 71B, 71C, etc. The signal representing the light output (and therefore representing the amount of energy in the initially incident gamma ray) is input to a serial string of a high bandwidth buffer amplifier 72A, 72B, 72C, etc., a pulse shaper 73A, 73B, etc. and an ADC 74A, 74B, etc. As can be seen, each SSPM supplies a signal to one serial string.

Similarly, the light produced by crystals 75A, 75B, 75C, etc. (when struck by a gamma ray) is detected and a signal representative thereof is produced by an associated SSPM 76A, 76B, 76C, etc. The signal representing the light output (and therefore representing the amount of energy in the impinging gamma ray) is input to a serial string of a high bandwidth buffer amplifier 77A, 77B, etc. a pulse shaper 78A, 78B, etc. and an ADC 79A, 79B, etc.

The crystals 70X (where X represents any letter, A, B, etc.) are considered a first subset and the crystals 75X are considered a second subset of all crystals (i.e., the crystals 70X and 75X).

The ADCs 74A, 74B, 79A, 79B etc. produce a digital signal representing the energy in the received gamma ray.

The signal from each SSPM 71A, 71B, 71C, etc. (representing the received gamma ray energy) is also input to an associated comparator 88A, 88B, 88C, etc. The comparator output signals are input to a TDC 140 for generating timing signals (as further described below) that are used to correct the energy signals and thereby reduce the Compton scattering effects in those energy signals. This correction allows for more accurate detection of coincident events and therefore the generation of a more accurate representation of the scanned tissue.

The signal from each SSPM 76A, 76B, 76C, etc. (representing the received gamma ray energy) is also input to an associated comparator 89A, 89B, 89C, etc. The comparator output signals are input to a TDC 142 for generating timing signals that are used to correct the energy signals by reducing the Compton scattering effects.

The timing signals from TDC 140 and 142 are input to an energy and timing correction element 145, which also receives the energy signals from the ADCs 74X, 79X Within the element 145 the timing signals correct the digitized energy signals. The corrected energy and timing signals are further processed, through elements well known in the art and illustrated generally as an image generation element 147 to generate the PET image on a display 149.

The inventors have determined that the probability of a gamma ray striking a crystal 70X and scattering to another crystal 70X is relatively low due to the distance between each crystal 70X, which is due to the intervening crystal 75X. But a gamma ray incident on a crystal 70X scattering to an adjacent crystal 75X has a relatively high probability. The various multiplexing schemes of the embodiments of the invention take advantage of this discovery.

Figure 6:
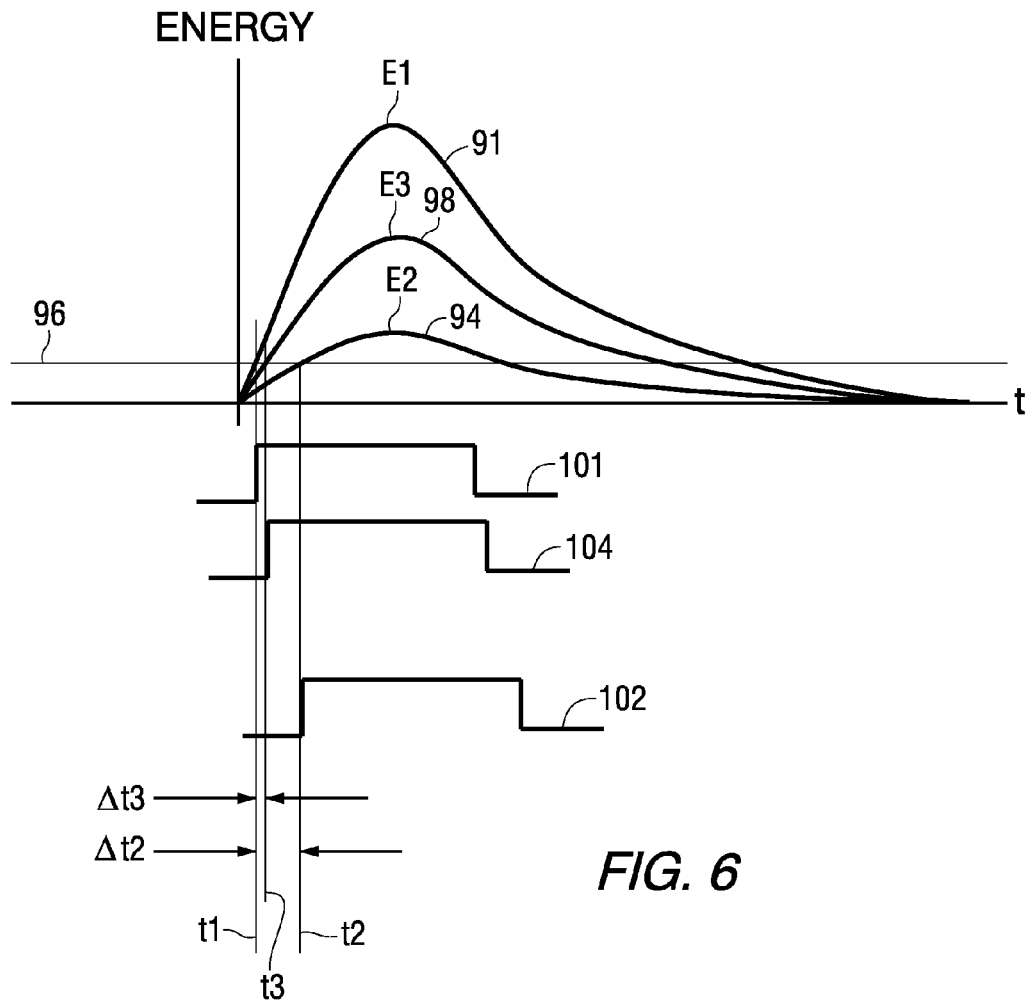
FIG. 6 is a graph of scintillation signals from unscattered and Compton scattered gamma rays.

Various possible walk correction scenarios will now be described. In FIG. 5, a gamma ray 122 (referred to as an initial or incident ray or beam) deposits all its energy into the single crystal 70A (no scattering) and the energy is represented by an output signal from the SSPM 71A. This output signal is depicted in FIG. 6 as an energy waveform 91. Although there has been no scattering for the gamma ray 122, there may still be a need for walk correction as the energy window is finite, but it is smaller than if a Compton scattering event had occurred since the range of energies is greater when Compton scattering occurs.

The signal 91 is processed through the comparator 88A to generate a pulse output signal 101, with the leading pulse edge of the pulse determined when the energy signal 91 (with an energy peak E1) crosses a threshold 96 at a time t1. With no scattering to proximate crystals, the timing signals from TDCs 140 and 142 include no other pulses that indicate a necessary timing correction. Thus there may not be a need to correct the energy signal in the energy and timing correction element 145.

A gamma ray 120 strikes the crystal 70B where the beam deposits some energy (the first energy deposit), as represented by an energy waveform or energy signal 94 (with an energy peak E2) in FIG. 6. The beam scatters to a crystal 75B and deposits the remaining energy (as represented by an energy waveform or energy signal 98 with an energy peak E3) there.

The energy signal 94 produced by the SSPM 71B represents the energy (the first deposit energy) deposited in the crystal 70B by the gamma ray 120. The signal 94 is input to the comparator 88B. At a time t2 the signal 94 crosses the threshold 96 and an output of the comparator 88B goes high, as illustrated by a comparator output pulse 102.

Ideally, the threshold 96 should be set at a very low level to find an initial rise in the signal 94. But noise generated in the electronic components requires setting the threshold at a slightly higher level to avoid noise effects on the comparator output.

The SSPM 76B produces the energy signal 98 (with the energy peak E3) for the ray scattered to the crystal 75B (the second deposit energy). At a time t3 the signal 98 crosses the threshold 96 and the output signal from the comparator 89B goes high, as represented by a comparator output pulse 104 in FIG. 6.

The relative peaks of the energy signals 94 and 98 represent a Compton scattered event, such that the peak of the scattered energy (as represented by the energy signal 98) is greater than the peak of the first deposited energy (as represented by the energy signal 94). However, the curves 94 and 98 may be reversed. The energy waveforms 94 and 98 and their relative values are merely exemplary.

The comparator output signal for the energy signal 94 is processed through the TDC 140 where the time t2 is converted to a digital value. The time t3 is converted to a digital value in the TDC 142. Advantageously, according to this embodiment, only two TDCs are required due to the segregation of the crystals/SSPMs into two groups (70X/71X and 75X/76X).

Both the values t2 and t3 are input to the energy and timing correction element 145, which also receives the energy signals from the ADCs 74X, 79X. The energy and timing correction element 145 determines either $\Delta t2$ or $\Delta t3$ (or both) (see FIG. 6) as a function of the value of the respective pulse height E2 and E3, as further described below. Alternatively, the values $\Delta t2$ and/or $\Delta t3$ can be determined by measuring the time from a common time reference to the time t2 and/or the time t3.

In any case, the determined value $\Delta t2$ and/or $\Delta t3$ is subtracted from the determined t2 and/or t3 values (the time when the respective energy waveform crossed the threshold 96). This operation yields a corrected value $t2'=t2-\Delta t2$ and/or $t3'=t3-\Delta t3$. Since the signal carried by each readout channel experiences different delays due to wire and trace length or device-to-device delay variations, and other channel-dependent variations, these signal delays should also be removed before calculating t2' and t3.' These delays are generally constant and do not change with time.

In PET scanners, there may also be a delay between the interaction of a gamma ray in the detector, and the time stamping of that event. For gamma rays that deposit the same energy in a given crystal, this delay is a constant and can be determined by a calibration method well know to one skilled in the art. This additional correction can be applied either before, after, or as part of the walk correction.

FIG. 6 depicts the energy waveform 91 for the unscattered ray 122 of FIG. 5. The waveform 91 serves as a timing reference since the $\Delta t2$ and $\Delta t3$ values are indicated from the common reference t1, which represents the time when the energy waveform 91 crossed the threshold 96. Thus according to FIG. 6, $t1=t2'=t3'$, as the effects of Compton scattering are not present in any of these three time values. This depiction in FIG. 6 is merely for explanatory convenience and other time points can be used as the timing reference for the $\Delta t2$ and $\Delta t3$ values.

Unscattered energy beams impinging one of the crystals 70X and 75X have an energy waveform similar to the energy waveform 91 for the unscattered beam 122 and cross the threshold 96 at t1. Thus by determining the threshold crossing time of the scattered energy waveforms (t2 and t3 in this example), determining the $\Delta t2$ and/or $\Delta t3$ values from the pulse height E2 and/or E3 (or determining $\Delta t2$ and/or $\Delta t3$ by measurement) and subtracting $\Delta t2$ and/or $\Delta t3$ from the corresponding t2 or t3, the real time values are corrected to an unscattered energy beam, for example as represented by the beam 122 (see FIG. 5) and its threshold crossing time t1. Removing the Compton scattering effects allows more accurate determination of the gamma rays that originated from the same annihilation event.

As described further below, several time difference values, including predetermined delays, are stored (in a look up table) within the energy and timing correction element 145 as a function of a pulse height. Thus once the pulse height E2 and/or E3 is determined, the associated time difference value (e.g., $\Delta t2$ and/or $\Delta t3$) can be determined from the look-up table (which provides the same information as a stored plot of E2 versus $\Delta t2$ and a plot of E3 versus $\Delta t3$). The t2 and t3 values will have been determined from the comparator outputs and thus the corrected values $t2'=t2-\Delta t2$ and/or $t3'=t3-\Delta t3$ can be calculated. In another embodiment, in lieu of using a lookup table or a plot, a functional relationship is determined from which $\Delta t2$ and/or $\Delta t3$ can be determined based on the pulse height E2 and/or E3.

For the case where the pulse shapes of the signals into the comparators 140 and 142 are substantially the same for interactions in all crystals of the PET scanner, all the crystals can use the same generalized function to calculate the walk corrections. If there are significant differences among the pulses from the crystals, individualized functions for the walk corrections can be generated and used. In either case, the function can be determined by measuring the change in the triggering of the comparator as a function of the energy deposited in a crystal using a method well know to one skilled in the art.

If the determined corrected values t2' and t3' are within a predetermined temporal interval, for example t2'−t3'≦2 ns, then the energy waveforms 94 and 98 are identified as originating from the same gamma ray (i.e., they are identified as an incident gamma ray and a Compton ray scattered from the incident ray). Also, the sum of E2 and E3 should be about 511 keV, i.e., the energy of the photon that impinged the crystal 70B in FIG. 5. Determining this sum can be a further check that the energy signals 94 and 98 originated from the same gamma ray. In any case, this determination is a prerequisite for correcting the t2 and t3 values as described above. It is known that random gamma rays can be emitted at the same time and such gamma rays can be rejected by one or both of the temporal window or energy sum tests. However, the rate of such random events is small.

Returning to FIG. 5, the corrected energy and timing signals from the element 145 are further processed through the image generation element 147 to generate the PET image on the display 149.

Generally, the value Δt3 is more accurate than the value Δt2 since the pulse height E3 is greater than the pulse height E2 and it is therefore preferable to use the value Δt3. It is expected that there is more uncertainty associated with the lower pulse height E2. In other embodiments, some combination of the values Δt2 and Δt3 can be used to correct the values t2 and t3. For example, a weight value can be applied to each of the values Δt2 and Δt3, where the weights can be 1/(variance (Δt2)) and 1/(variance (Δt3)), the pulse height E2 and E3, or sqrt(E2) and sqrt(E3), respectively.

Also, if the values of E2 or E3 are approximately 511 keV, no correction for Compton scattering is required. If the values of E2 and E3 are about equal, then either can be used for the scattering correction with approximately similar results.

FIG. 5 illustrates one initial gamma ray that deposits energy into two crystals. It is possible, but not illustrated, that a single gamma ray can deposit energy into more than two crystals due to successive Compton scattering events. Processing such a double scattering event is achieved using the same principles as described herein.

Note that the arrival time of the signals 94 and 98 in FIG. 6 is the same; both curves begin at t=0. The delay in the resulting pulses 102 and 104 is due to the fixed threshold 96 of the comparators 88C and 88D and the crossing of that threshold at different times due to the difference in the initial slopes and peak values of the energy signals 94 and 98.

Figure 1:
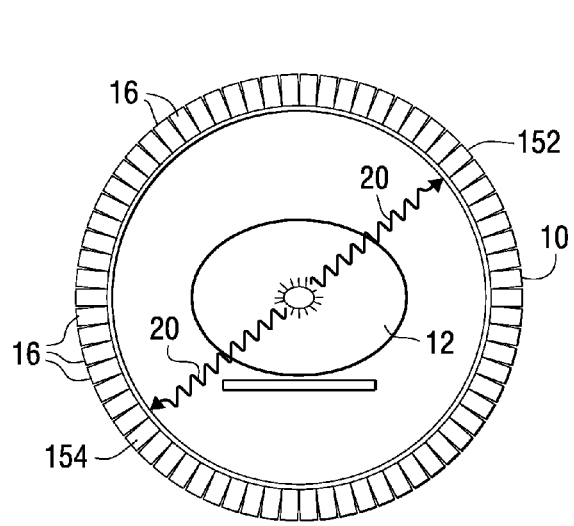
FIGS. 1 and 2 illustrate side and perspective views of a PET detector ring.
Figure 2:
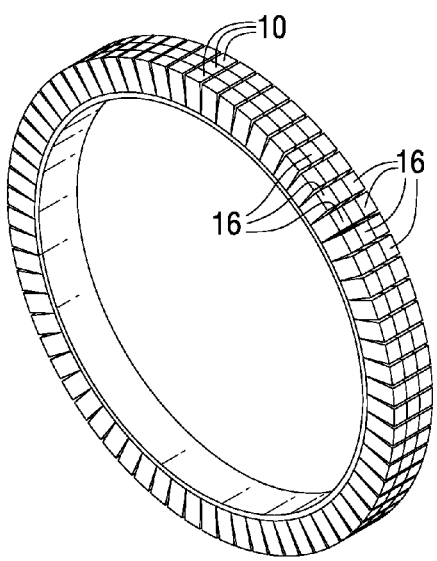
Figure 3:
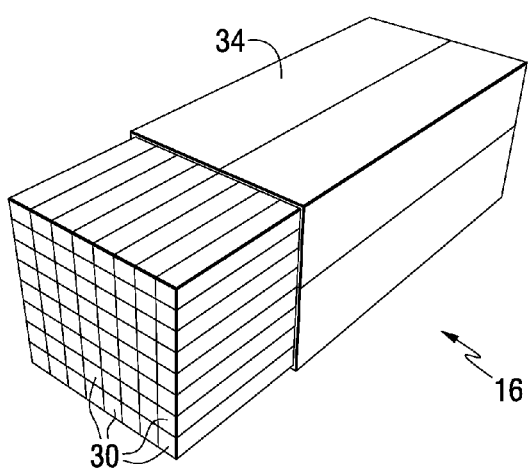
FIG. 3 illustrates a block detector of the ring of FIGS. 1 and 2.

After all the Compton scattering events have been corrected as described herein, it is then possible, and more accurate, to compare the arrival times from the readout channels associated with the scintillation crystals, such as the crystals 152 and 154 illustrated in FIG. 1, to determine the events that are coincident in time and thus represent gamma rays created during the same annihilation event.

Figure 7:
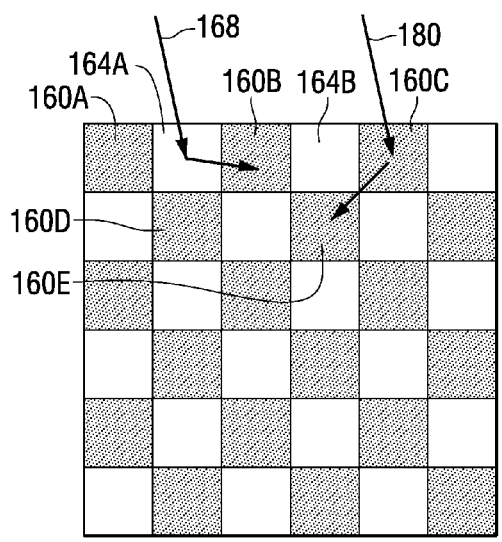
FIGS. 7, 8 and 9 illustrate three different crystal patterns multiplexed according to different embodiments of the invention.

FIG. 7 illustrates a relatively small array of crystals-SSPMs for depicting one embodiment of the present invention. Each SSPM is connected to a comparator, such as illustrated in FIG. 5. One feature of the present invention is the multiplexing of the signals from the comparators to the TDCs. For example, as applied to the crystal array of FIG. 7, alternating comparators are connected to corresponding first or second TDCs. Thus crystals 160A, 160B, 160C, etc. are members of a first crystal group and are connected to a first TDC (such as the TDC 140 in FIG. 5) and alternating crystals 164A, 164B, 164C are members of a second crystal group and are connected to a second TDC (such as the TDC 142 in FIG. 5).

In FIG. 7, a gamma ray 168 directly strikes the crystal 164A and scatters onto the horizontally oriented crystal 160B. More generally, certain gamma rays striking any crystal 164X may scatter to any crystal 160X. A gamma ray 180 directly impinges upon the crystal 160C and scatters to the diagonally oriented crystal 160E. More generally, certain gamma rays striking any crystal 160X may scatter to another crystal 160X.

In the embodiment of FIG. 7 only two TDCs are utilized. All crystals designated 160X are multiplexed to a first TDC and all crystals designated 164X are multiplexed to a second TDC.

As described above, the energy signals 94 and 98 are used to correct the time parameters t2 and t3, for gamma rays striking one of the crystals 164X and scattering to one of the other crystals 160X. Thus the arrangement illustrated in FIG. 7 can determine the scattering effects and can correct the scattering effects for the gamma ray 168.

The gamma ray 180 impinges on the crystal 160C and scatters diagonally to the crystal 160E. Both the crystal 160C and 160E are multiplexed to the same TDC. It is generally believed a single state-of-the-art TDC cannot receive and digitize two signals that are closer in time than about 50 ns. Thus the timing values (t2 and t3 of FIG. 6) cannot be determined from a single TDC and the Compton scattering cannot be corrected for the ray 180.

In another embodiment, the number of TDCs and comparators is equal to the number of crystals to determine and digitize the timing signals. Such an arrangement may therefore be characterized as an individual readout channel for each crystal and is capable of digitizing two or more timing signals that are closer in time than the timing resolution of an individual TDC.

Figure 8:
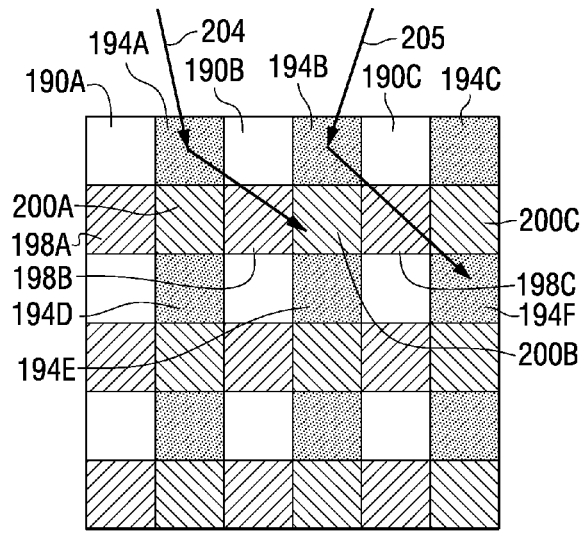

FIG. 8 illustrates another array of crystals for depicting another embodiment of the present invention that overcomes certain correction limitations inherent in the FIG. 7 multiplexing scheme. In this embodiment the crystal array is subdivided into four crystal groups (or subsets), each one represented by a different shading/cross-hatching scheme. All SSPMs are connected to a comparator, (as in FIG. 5) and each comparator supplies input signals to one of four different TDCs. The crystal groups are represented by four reference characters 190X, 194X, 198X and 200X (where X again denotes any letter).

The crystals in each crystal group are connected to a different TDC. With four crystal groups and four corresponding TDCs, the probability of a non-resolvable scattering event is lower than for the embodiment presented in FIG. 7. According to the FIG. 8 embodiment, scattering of a gamma ray 204 from a crystal 194A to a crystal 200B can be resolved since these two crystals feed two different TDCs. But scattering of a gamma ray 205 from a crystal 194B to a crystal 194F cannot be corrected since both crystals feed the same TDC. Thus the digital values of these timing signals cannot be determined.

Figure 9:
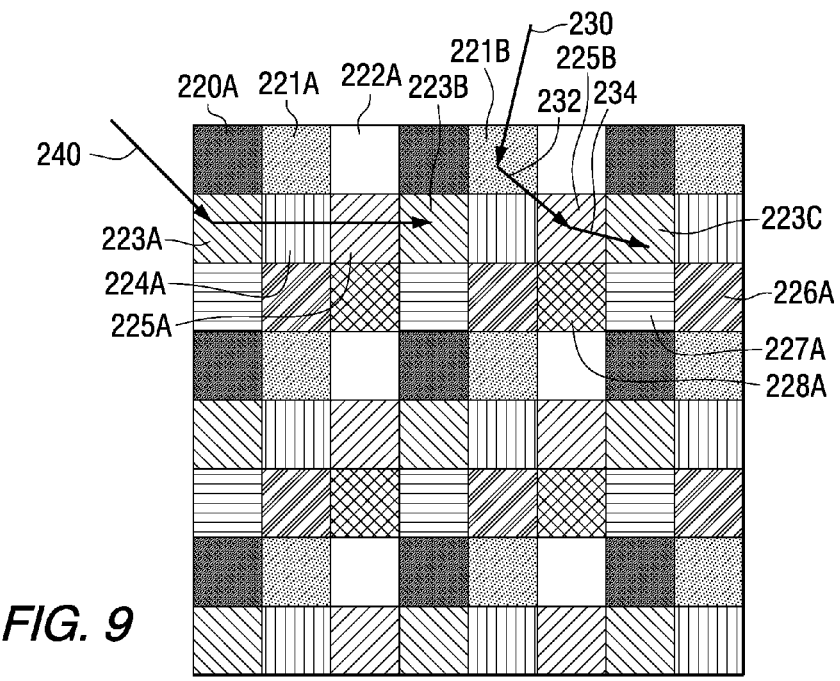

State-of-the-art crystals are becoming increasingly smaller and certain crystals are approximately 2 or 3 mm square. The embodiment of FIG. 8 may not resolve all gamma scattering to proximate crystals. FIG. 9 depicts a crystal array subdivided into nine different crystal groups identified by different shading/cross hatching and by a different reference character: 220X, 221X, 222X, 223X, 224X, 225X, 226X, 227X, and 228X. This embodiment requires nine TDCs, one TDC for each crystal group, i.e., one TDC for all crystals 220X, one TDC for the 221X crystals, etc. An embodiment with nine TDCs (achieved by multiplexing multiple crystal signals to a single TDC) operates at about ten times less power consumption than a system employing one TDC for each crystal.

An initial gamma ray 230 strikes a crystal 221B, scatters to a crystal 225B as ray 232, and scatters again to a crystal 223B as a ray 234. Since each of these crystals is a member of a different crystal group and therefore supplies a signal to a different TDC, the energy in the ray 230 can be corrected to eliminate the effects of Compton scattering. However a ray 240 striking a crystal 223A and scattering to a crystal 223B cannot be corrected as both crystals 223A and 223B are connected to the same TDC.

As explained elsewhere herein, the crystals within each crystal group are selected such that scattering from a crystal of one group has a relatively high probability of striking a crystal in another crystal group. The probability that a gamma ray scatters from a crystal that is a member of a first crystal group to a crystal that is a member of a second crystal group is higher for the FIG. 9 embodiment than for the FIG. 7 or 8 embodiments. By multiplexing the energy signals from each crystal within a crystal group to one TDC, multiplexing the signals from other crystal groups to other TDCs, and judiciously selecting the crystals within each group based on the scattering probabilities, the effects of most Compton scattering events can be corrected.

By using a single TDC for all crystals in the same group, the power consumed by the readout channel elements, when compared to the prior art scheme that requires one TDC for each readout channel, is drastically reduced. But this inventive scheme retains the same information (timing and gamma ray energy) as in the prior art to perform the Compton scattering correction.

As illustrated by the crystal grouping progression depicted in FIGS. 7-9, as more crystal groups are added more Compton scattering events can be corrected. The specific scheme employed, i.e., number of crystal groups and like number of associated TDCs, is dependent on the specific operational details of the PET scanner and the desired scan resolution, which affects the crystal spacing and thereby the number of crystal groups preferred to limit the scattering effects. Most PET scanners employ 4 mm crystals and thus the scheme illustrated in FIG. 8 may be adequate to correct substantially all of the Compton scattering effects. Also, since the conventional PMT readout scheme employs four readout channels, the use four crystal groups (i.e., four readout channels) as depicted in FIG. 8 permits relatively easy integration of the present invention into existing PET scanners.

According to yet another embodiment of the invention, the non-linear response of each SSPM 71X/76X can be corrected using the measured energies, E1, E2, E3, as shown in FIG. 6, using the ADCs for energy measurement combined with the TDC for timing measurement. Each SSPM comprises a fixed number of micro-cells. This fixed number of micro-cells, for example, 3000 cells, can measure gamma ray energy linearly if the number of generated visible photons is low, for example, from 1 to about 1000 photons. If the gamma ray generates many more visible photons, for example greater than about 2000, a SSPM with a limited number of micro-cells may saturate and therefore may not linearly measure the gamma ray energy. Thus the ability to linearly measure the gamma ray energy is dependent on the number of incoming photons relative to the number of micro-cells in the SSPM.

This non-linearity of the SSPM can be corrected, in a manner similar to the timing correction described above, if the energy deposited in each crystal/SSPM is measured individually as depicted in FIG. 6. The correction can be implemented using a response lookup table of incident energy vs. measured energy for each crystal/SSPM. The sum of the energy after correction represents 511 keV correctly when there is a Compton scattering between crystals. But the sum for uncorrected energy values will not accurately represent the total energy. Although more micro-cells in each SSPM can more accurately measure the energy and thus reduce the need for this correction step, the additional micro-cells will reduce the effective detector area. There is therefore a trade-off between the number of micro-cells in each SSPM and the effective detector area.

Another embodiment of the present invention uses a multiplexing scheme to limit not only the number of required TDCs, but also the number of required ADCs. This embodiment further reduces the power consumption since the ADCs also consume a substantial amount of power.

Figure 10:
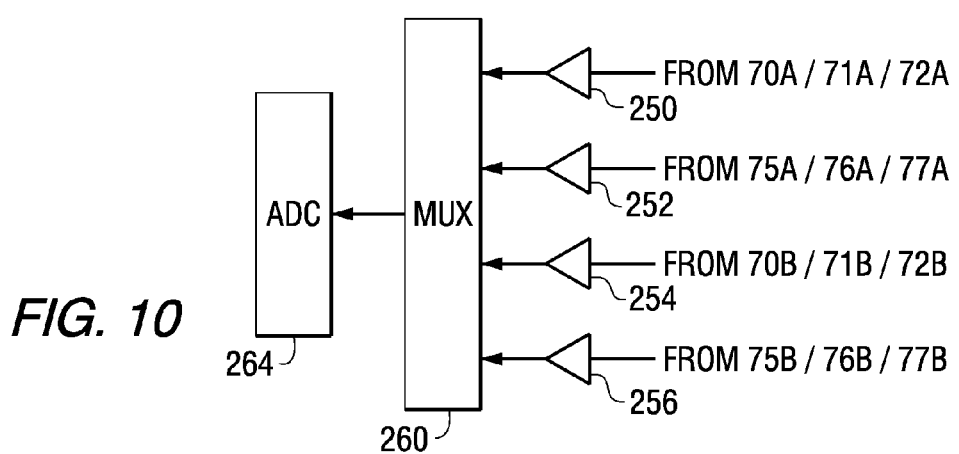
FIGS. 10-12 illustrate various multiplexing circuits for the gamma ray energy signals according to different embodiments of the invention.

It is noted that connection of the ADCs may not be directly related to any of the checkerboard patterns (for determining timing signals) of FIGS. 7-9, although the pattern may determine the allowed connections. The checkerboard pattern applies specifically only to the crystals that are multiplexed to a common TDC to obtain the timing signals, but the connections to the ADCs must account for measurement of the energy deposited in each of the checkerboard subsets separately. FIG. 10 illustrates a technique for reducing the number of ADCs, by multiplexing a plurality of SSPM output signals from the pulse shapers 73X and 78X.

Returning to FIG. 5 each readout channel includes a dedicated ADC, e.g., ADCs 74X (for readout channels comprising the crystals 70X) and ADCs 79X (for readout channels comprising the crystals 75X). In an embodiment of FIG. 10, the output signal from a readout channel (comprising the crystal 70X, the SSPM 71X and the buffer amplifier 72X or a readout channel comprising the crystal 75X, the SSPM 76X and the buffer amplifier 77X) is input to a pulse shaper 250, 252, 254 or 256. The output signals from the pulse shapers 250, 252, 254 and 256 are multiplexed in a multiplexer 260 and supplied to an ADC 264. Only four signals are illustrated as feeding a single multiplexer 260, but more or fewer signals can feed a single multiplexer. The analog output signal from the multiplexer 260 is converted to a digital signal in the ADC 264. Thus the multiplexed ADC scheme of FIG. 10 requires fewer ADCs than the scheme of FIG. 5. A reduction in power consumption is one advantage of the FIG. 10 embodiment.

Because the energy signals are multiplexed in the multiplexer 260, it is necessary to retain an identification of the origin (i.e., the originating crystal/SSPM) of the energy signal. The energy signal from the ADC 264 therefore includes a representation of the energy in the impinging gamma ray and an identification of the crystal/SSPM that received the gamma ray. For example, the signal from the pulse shaper 250 (and therefore from the crystal/SSPM 70A/71A) can be identified with identification numeral 1 and the signal from the pulse shaper 252 (and therefore from the crystal/SSPM 75A/76A) can be identified with identification numeral 2. Therefore the first digitized energy signal from the ADC 264 includes a representation of the energy impinging the crystal 70A and the identification numeral 1.

When the pulse shaper 250 receives a signal, an element of the multiplexer 260 is activated to include the proper identification information in the multiplexed signal. The ADC 264 then digitizes the signal from the pulse shaper 250 and annexes the identifier to the digital signal. This technique provides the energy timing and correction element 145 with a digital representation of the energy signal and an identification of the impinged crystal to be used for walk correction.

Energy signals from the remaining crystals are identified in a similar manner. Operation of the ADC 264 and the TDCs 140/142 should be synchronized to match the timing information from the TDCs with the energy information from the pulse shapers 250, 252, 254, 256. The synchronization can be accomplished by a system-wide clock, operating, for example at 40 MHz or 100 MHz. As an alternative to the described synchronization scheme, both the timing and energy signals can be identified to ensure that the timing information is coupled with the associated energy information.

The walk correction calibration lookup table of the present invention can be generated by one isotope timing calibration utilizing different energy windows. A simple lookup table scheme can be generated as follows. For each crystal, the TDC and ADC data is collected during one isotope timing calibration. Then a plot showing the correlation of TDC vs. ADC is fitted to the data to find the correction factor as a function of energy, including channels delays. This correction function is used to calculate the timing correction, $\Delta t$ at a given energy level, for Compton scattering events. This function can be stored within the PET scanner electronics with an identification of the crystal/SSPM to which it pertains as a lookup table (in a field programmable gate array, for example). When a scattering event occurs during a patient scan, the correction factor can be obtained or calculated from the look up table, depending on the energy level and the applicable crystal/SSPM. The correction factor is then used to correct the timing output as described above.

Figure 11:
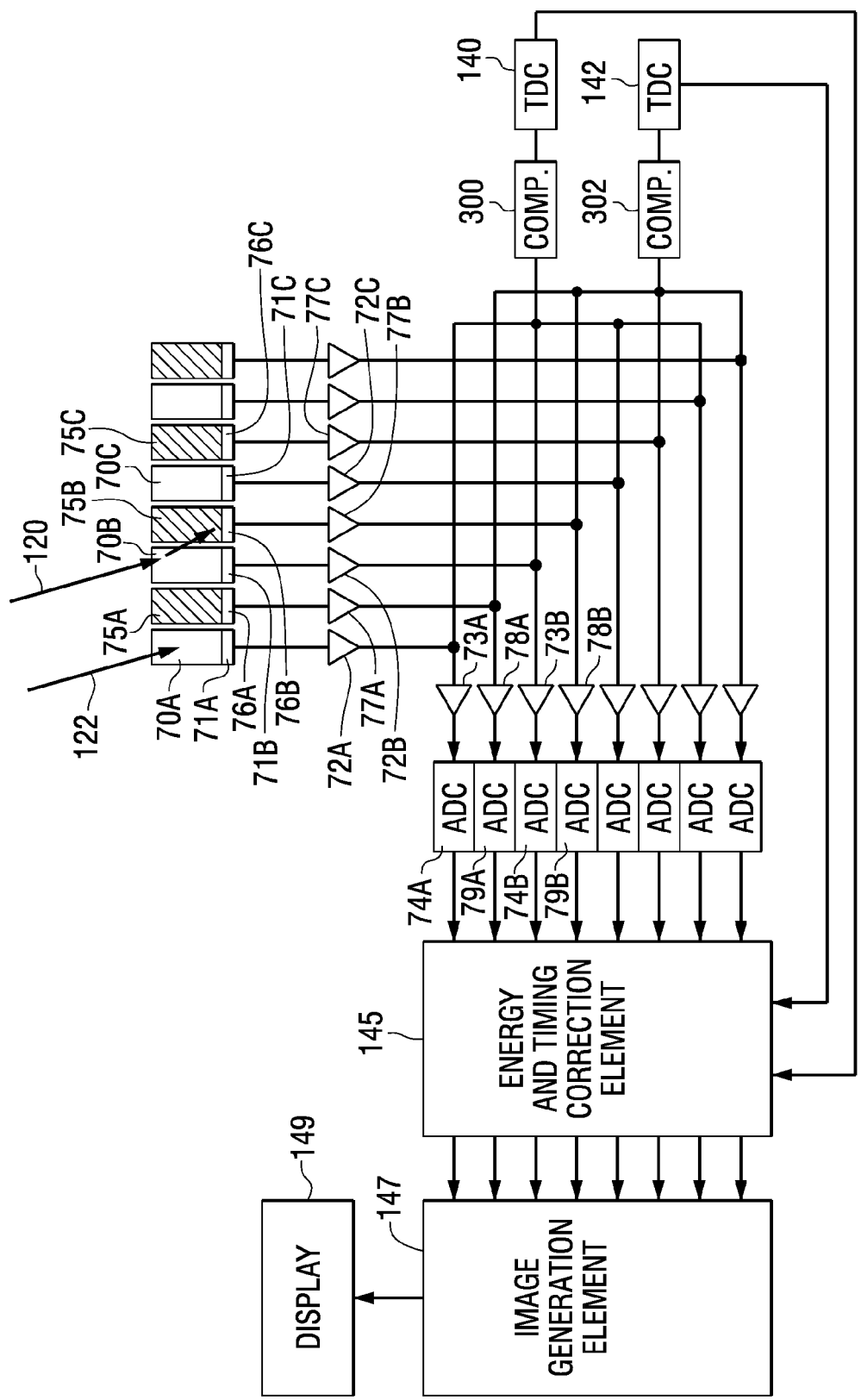

In another embodiment of the invention, in a similar fashion to combining a plurality of comparator outputs to a single TDC input (as illustrated in FIG. 5), the output signals from a plurality of buffer amplifiers 72X can combined into a first comparator followed by a first TDC; and the output signals from a plurality of buffer amplifiers 77X can be combined into a second comparator followed by a second TDC. This embodiment reduces the number of required comparators, saving physical space and power. With reference to FIG. 11, signals from the crystals/SSPMs/buffer amplifiers 70X/71X/72X can be combined to feed a comparator 300 that in turn feeds the TDC 140. Similarly, signals from the crystals/SSPMs/buffer amplifiers 75X/76X/77X can be combined to feed a comparator 302 that in turn feeds the TDC 142. This embodiment reduces the number of comparators. The viability of this embodiment depends on dark current noise generated within the SSPMs. As SSPMs are improved to generate less noise, implementation of this embodiment becomes more practical.

Figure 12:
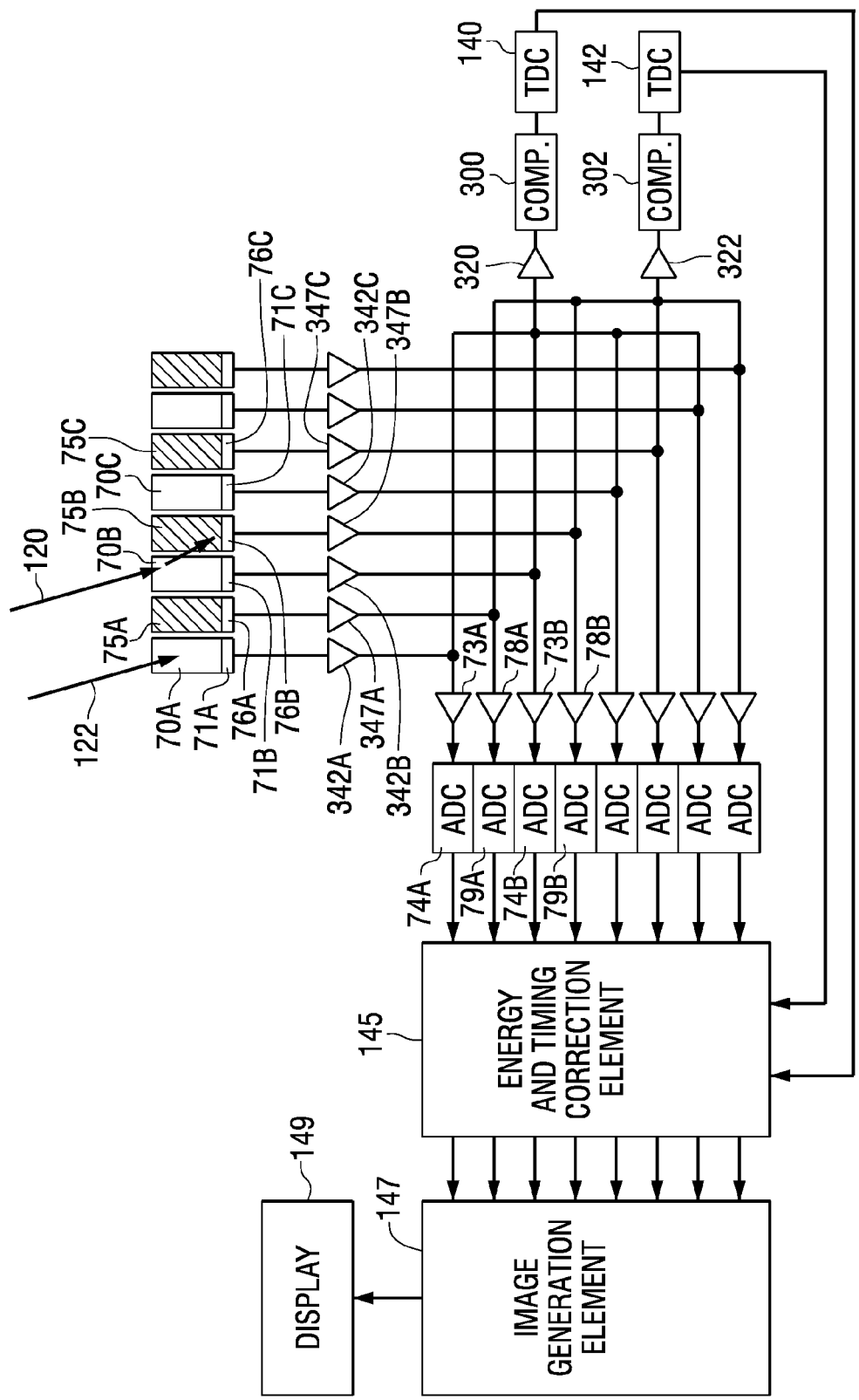

In yet another embodiment the number of buffer amplifiers can be reduced by combining all signals from the crystals/SSPMs 70X/71X to feed a single buffer amplifier 320 (see FIG. 12) and combining all signals from the crystals/SSPMs 75X/76X to feed a single buffer amplifier 322. However, since each SSPM exhibits a capacitance greater than about 100 pF, compared with less than about 10 pF for PMTs, connecting the SSPMs together according to this embodiment may further increase the capacitance and thereby distort the timing information present in each SSPM output signal.
CLAIM For the FIG. 12 embodiment, the buffer amplifiers 72X/77X may comprise an emitter follower or a current mirror (i.e., a one or two transistor amplifier) to isolate the large capacitance of the SSPMs. The emitter follower amplifier has a gain of one, isolates the input capacitance from the output, and operates over a wide bandwidth to maintain the integrity of the input signal. The buffer amplifiers 320 and 322 may each be followed by a high gain amplifier, not shown in FIG. 12, followed by the comparators 300 and 302 for determining the required timing parameters.

Although the embodiments of the invention have been described with respect to imaging bodily organs, the teachings are applicable to other volumetric objects. While the various embodiments of the invention have been described in what is presently considered to be a preferred embodiment, many variations and modifications will become apparent to those skilled in the art. Accordingly, it is intended that the inventions not be limited to the specific illustrative embodiments but be interpreted within the full spirit and scope of the appended claims.

This written description of the embodiments of the invention uses examples to disclose the inventions, including the best mode, and also to enable any person skilled in the art to make and use the inventions. The patentable scope of the inventions are defined by the claims, and may include other examples that occur to those skilled in the art. Such other examples are intended to be within the scope of the claims if they have structural elements or process steps that do not differ from the literal language of the claims, or if they include equivalent structural elements or process steps with insubstantial differences from the literal language of the claims.

What is claimed is:

1. A method for producing a PET image of a tissue using a PET scanner, the scanner comprising a plurality of scintillation crystals and a plurality of detectors, the method comprising:
   forming a first crystal group including a first subset of the plurality of crystals;
   forming a second crystal group including a second subset of the plurality of crystals, wherein crystals comprising the first crystal group are different from crystals comprising the second crystal group;
   converting a first beam striking one or more crystals of the first crystal group to a first electrical signal;
   converting a second beam striking one or more crystals of the second crystal group to a second electrical signal, wherein the second beam is scattered from the first beam;
   determining one or both of a first and a second timing relationship, wherein the first timing relationship is a time interval between a value of the first electrical signal and a time reference, and the second timing relationship is a time interval between a value of the second electrical signal and the time reference;
   correcting the second electrical signal to produce a corrected second electrical signal using a correction factor derived from at least one of the first and the second timing relationships to compensate for energy in the second signal scattered from the first signal; and
   creating an image of the tissue using the corrected second electrical signal.

2. The method of claim 1 further comprising providing a digital representation of the second electrical signal and of one or both of the first and the second timing relationship.

3. The method of claim 1 wherein the number of crystals is equal to the number of detectors.

4. The method of claim 1 wherein the crystals of the first subset are mutually exclusive with the crystals of the second subset.

5. The method of claim 1 wherein the time reference is derived from an unscattered beam.

6. The method of claim 1 wherein the time reference is a time t1 when an unscattered beam crosses a threshold, and wherein the first timing relationship is a time interval between t1 and the first electrical signal crossing the threshold, and wherein the second timing relationship is a time interval between t1 and the second electrical signal crossing the threshold.

7. The method of claim 1 wherein a sum of energy of the first beam and energy of the second beam is about 511 keV.

8. The method of claim 1 wherein if the first and the second electrical signals occur within a predetermined time window, then the first and second beams originated from a same incident gamma ray, and wherein the step of correcting further comprise correcting the first electrical signal to produce a corrected first electrical signal.

9. The method of claim 1 wherein the step of determining further comprises determining one or both of the first and the second timing relationships responsive to a signal parameter of the corresponding first electrical signal and the second electrical signal.

10. The method of claim 9 wherein the signal parameter comprises a pulse height.

11. The method of claim 9 wherein the step of determining comprises determining one of the first and the second timing relationships using the first or the second electrical signal having a greater magnitude.

12. The method of claim 1 wherein the correction factor comprises a weighted combination of the first and the second timing relationships, with the weights determined by parameters associated with the first and the second electrical signals.

13. The method of claim 12 wherein the parameters comprise one or more of a variance of each of the first and the second timing relationships, a pulse height of each of the first and second electrical signals, and a square root of each of the first and the second timing relationships.

14. The method of claim 1 wherein the step of determining comprises using a look up table indexed according to a signal parameter of the first and the second signals, wherein the lookup table provides the first and the second timing relationships.

15. The method of claim 1 wherein the step of determining further comprises developing a first functional relationship between signal parameters of the first electrical signal and first timing relationships and a second functional relationship between signal parameters of the second electrical signal and second timing relationships, and using the respective first and second functional relationships to determine the first and the second timing relationships responsive to a signal parameter of the respective first and second electrical signals.

16. The method of claim 1 wherein the step of determining further comprises compensating for channel dependent timing variations.

17. The method of claim 1 wherein the value of the first electrical signal and the value of the second electrical signal each comprise a time when the corresponding first signal and second signal cross a threshold.

18. The method of claim 1 wherein the step of determining further comprises:
a first comparator producing a first output pulse when the first electrical signal crosses a threshold;
a second comparator producing a second output pulse when the second electrical signal crosses the threshold; and
wherein a difference between a leading edge of the first output pulse and a time when an energy signal representing an unscattered beam crosses the threshold comprises the first timing relationship, and wherein a difference between a leading edge of the second output pulse and the time when the energy signal representing the unscattered beam crosses the threshold comprises the second timing relationship.

19. The method of claim 1 wherein crystals are assigned to the first or to the second crystal group according to the probability of beams striking a crystal in the first crystal group scattering to a crystal in the second crystal group.

20. The method of claim 1 wherein the steps of converting a first and a second beam each further comprise compensating for non-linear responses of solid state photomultipliers that convert the first and second beams to respective first and second electrical signals.

21. The method of claim 20 wherein the non-linear responses of the solid state photomultiplier that converts the first beam to the first electrical signal are compensated responsive to a signal parameter of the first electrical signal, and the non-linear responses of the solid state photomultiplier that converts the second beam to the second electrical signal are compensated responsive to a signal parameter of the second electrical signal.

22. The method of claim 20 wherein the step of compensating for non linear responses comprises compensating for at least one of non linear energy responses and non linear timing responses.

23. A method for producing a PET image of a tissue using a PET scanner, the scanner comprising a plurality of scintillation crystals and a plurality of detectors, the method comprising:
forming a first crystal group including a first subset of the plurality of crystals;
forming a second crystal group including a second subset of the plurality of crystals, wherein crystals comprising the first crystal group are different from crystals comprising the second crystal group;
converting beams striking one or more crystals of the first crystal group to a like number of electrical signals;
determining a time of occurrence of the leading edge of each electrical signal;
determining corrected electrical signals by correcting the time determined at the determining step according to a respective amplitude of each electrical signal; and
creating an image of the tissue using the corrected electrical signals.

24. An apparatus for producing a PET image using a PET scanner, the apparatus comprising:
scintillation crystals segregated into a plurality of mutually exclusive crystal groups;
detectors, one detector coupled to each scintillation crystal, each detector for producing an energy signal responsive to the energy in a gamma ray striking a crystal associated with the detector;
comparators responsive to the detectors, each comparator for producing a signal representative of a time when a energy signal crosses a threshold;
a number of time-to-digital converters equal to the number of crystal groups, wherein a signal produced by each comparator is supplied as an input to the time-to-digital converter for the respective crystal group for producing a digital timing signal representative of the time when the energy signal crosses the threshold; and
a correction element responsive to the energy signal and to the digital timing signal for correcting the energy signal responsive to the digital timing signal.

25. The apparatus of claim 24 wherein a number of comparators is equal to a number of detectors.

26. The apparatus of claim 24 wherein a plurality of energy signals are input to a single comparator, and wherein an output signal from the comparator is input to a time-to-digital converter.

27. The apparatus of claim 24 wherein a number of comparators equals the number of crystal groups, and wherein all energy signals from a crystal group are input to a single comparator.

28. The apparatus of claim 27 further comprising a buffer amplifier for each crystal group, each buffer amplifier interposed between the detectors associated with the crystals of a crystal group and the comparator associated with the crystal group.

29. The apparatus of claim 24 wherein the plurality of groups comprise four groups and each crystal is a member of one of the four groups, but not a member of more than one group.

30. The apparatus of claim 24 wherein crystals are assigned to each group such that a probability of a gamma ray striking a crystal in a first group and scattering to a crystal in a different group is greater than a probability of a gamma ray striking a crystal in the first group and scattering to another crystal in the first group.

31. The apparatus of claim 24 wherein each one of the plurality of detectors comprises a solid state photomultiplier detector.

32. The apparatus of claim 24 further comprising a multiplexer for receiving an analog form of the energy signal from each of the detectors and multiplexing received energy signals to provide one energy signal at any time to an analog-to-digital converter for providing a digital energy signal responsive to the one energy signal, wherein the digital energy signal further comprises an indication of the detector producing the analog form of the energy signal.

* * * * *